US009443707B2

(12) United States Patent
Hayden et al.

(10) Patent No.: US 9,443,707 B2
(45) Date of Patent: Sep. 13, 2016

(54) METHOD AND APPARATUS FOR TRANSPORTING SAMPLES IN A MASS SPECTROMETER

(71) Applicant: Virgin Instruments Corporation, Marlborough, MA (US)

(72) Inventors: Kevin Hayden, Newton, MA (US); Marvin L. Vestal, Framingham, MA (US)

(73) Assignee: Virgin Instruments Corporation, Marlborough, MA (US)

( * ) Notice: Subject to any disclaimer, the term of this patent is extended or adjusted under 35 U.S.C. 154(b) by 0 days.

(21) Appl. No.: 15/044,934

(22) Filed: Feb. 16, 2016

(65) Prior Publication Data

US 2016/0225596 A1 Aug. 4, 2016

Related U.S. Application Data

(63) Continuation-in-part of application No. 14/611,260, filed on Feb. 1, 2015.

(51) Int. Cl.
*H01J 49/04* (2006.01)
*H01J 49/40* (2006.01)

(52) U.S. Cl.
CPC ........ *H01J 49/0409* (2013.01); *H01J 49/0495* (2013.01); *H01J 49/40* (2013.01)

(58) Field of Classification Search
USPC .................. 250/288, 287, 441.11, 442.11
See application file for complete search history.

(56) References Cited

U.S. PATENT DOCUMENTS

| 5,841,136 A | 11/1998 | Holle et al. |
| RE39,353 E | 10/2006 | Vestal |
| 7,282,707 B1 * | 10/2007 | Zanon ............... H01J 49/0409 250/281 |
| 9,214,323 B1 | 12/2015 | Vestal et al. |

* cited by examiner

*Primary Examiner* — Kiet T Nguyen
(74) *Attorney, Agent, or Firm* — Kurt Rauschenbach; Rauschenbach Patent Law Group, LLC (57) ABSTRACT

A sample plate handling system for a time-of-flight mass spectrometer includes a transport chamber and a mass spectrometer chamber that is mechanically coupled to transport chamber. A vacuum chamber is coupled through a bypass valve to the transport chamber. A two-dimensional translation stage is positioned in the mass spectrometer chamber. A sample plate transporter is mounted on the two-dimensional translation stage. A first portion of the sample plate transporter is mechanically attached to the two-dimensional translation stage. A second portion of the sample plate transporter defines a sample plate receiver that is positioned in the transport chamber. A sealing orifice located between the first and the second portions connects the transport chamber and the mass spectrometer chamber. A motion of the two-dimensional translation stage in one direction aligns the sample plate transporter with the sealing orifice and a motion of the two-dimensional translation stage in the other direction moves the sealing surface of the sample plate transporter to engage the sealing orifice, thereby preventing gas flow between the mass spectrometer chamber and the transport chamber.

37 Claims, 8 Drawing Sheets

METHOD AND APPARATUS FOR TRANSPORTING SAMPLES IN A MASS SPECTROMETER

CROSS-REFERENCE TO RELATED APPLICATION

This application is a continuation-in-part of U.S. patent application Ser. No. 14/611,260, entitled "Method and Apparatus for Transporting Samples in a Mass Spectrometer" filed on Feb. 1, 2015. The entire specification of U.S. patent application Ser. No. 14/611,260 is herein incorporated by reference.

INTRODUCTION

Many modern mass spectrometers that analyze samples deposited on a solid surface require that the pressure inside the ion source be sufficiently low to ensure that ions produced by the ionization process only rarely collide with neutral molecules present in the system. Such mass spectrometers require a pressure inside the ion source to be less than $10^{-6}$ atmospheres (one atmosphere equals 760 Torr). These mass spectrometers often require a pressure inside the ion source to be $10^{-5}$ Torr or below. Vacuum pumps used for achieving very low pressure are well known in the art. The time required for achieving a given vacuum level is limited by the various system and vacuum pump parameters, such as the vacuum pumping speed, the volume of the vacuum chamber being evacuated, and contributions from contaminants present on inner walls of the vacuum chamber that may vaporize at rates that are comparable to the speed of the vacuum pump. These parameters also limit the ultimate pressure that can be achieved in the ion source and vacuum chamber.

In some prior art mass spectrometers, the ion source chamber is separated from the mass analyzer chamber with a gate valve connecting them. When the gate valve is open, ions and neutral molecules may move freely between the two chambers. When the gate valve is closed, the vacuum levels and pumping speeds of the two chambers are independent, but the system is inoperative because ions are not transmitted. When a mass spectrometry analysis is completed, the gate valve is typically closed and the ion source chamber is typically vented to atmospheric pressure. The plate is ejected and a new plate is then loaded for additional analysis. The ion source chamber is then evacuated to the required vacuum pressure, at which point the gate valve is opened and analysis of the samples on the new plate may begin. The mass spectrometer is not operating during this vent/evacuate cycle, which, in some cases, may take as long as, or longer than, the time required to analyze the samples, leading to poor utilization of the instrument.

U.S. patent application Ser. No. 14/475,528, entitled "Method and Apparatus for Transporting Sample Plates Between Chambers of a Mass Spectrometer," which is assigned to the present assignee, describes a mass spectrometer having a sample plate handling system that includes a sample plate with samples of interest on one surface of the sample plate. The entire specification of U.S. patent application Ser. No. 14/475,528 is incorporated herein by reference. This patent application describes a sample plate handling system for a time-of-flight mass spectrometer that includes a sample plate for supporting samples for analysis. A first sample plate receiver is positioned in a first chamber. First and second sample plate receivers are positioned in a second chamber. A first gate valve isolates the first and second chambers when closed and allows transfer of sample plates between the first sample plate receiver in the first chamber and one of the first and second sample plate receivers in the second chamber when the first gate valve is open. A first linear extender pushes a sample plate from the first sample plate receiver in the first chamber to the first sample plate receiver positioned in the second chamber, and then retracts a second sample plate from the second sample plate receiver positioned in the second chamber and transports the second sample plate to the first sample plate receiver in the first chamber. A first sample plate receiver is positioned in a third chamber. A second gate valve isolates the third chamber from the second chamber when closed, and allows transfer of sample plates between the first sample plate receiver in the third chamber and one of the first and second sample plate receivers in the second chamber when the second gate valve is open. A second linear extender pushes a sample plate from the first sample plate receiver in the third chamber to the first sample plate receiver positioned in the second chamber, and then retracts the second sample plate from the second plate receiver positioned in the second chamber and transports it into the third chamber.

BRIEF DESCRIPTION OF THE DRAWINGS

The present teaching, in accordance with preferred and exemplary embodiments, together with further advantages thereof, is more particularly described in the following detailed description, taken in conjunction with the accompanying drawings. The skilled person in the art will understand that the drawings, described below, are for illustration purposes only. The drawings are not necessarily to scale, emphasis instead generally being placed upon illustrating principles of the teaching. The drawings are not intended to limit the scope of the Applicant's teaching in any way.

DESCRIPTION OF THE VARIOUS EMBODIMENTS

Reference in the specification to "one embodiment" or "an embodiment" means that a particular feature, structure, or characteristic described in connection with the embodiment is included in at least one embodiment of the teaching. The appearances of the phrase "in one embodiment" in various places in the specification are not necessarily all referring to the same embodiment.

It should be understood that the individual steps of the methods of the present teachings may be performed in any order and/or simultaneously as long as the teaching remains operable. Furthermore, it should be understood that the apparatus and methods of the present teachings can include any number or all of the described embodiments as long as the teaching remains operable.

The present teaching will now be described in more detail with reference to exemplary embodiments thereof as shown in the accompanying drawings. While the present teachings are described in conjunction with various embodiments and examples, it is not intended that the present teachings be limited to such embodiments. On the contrary, the present teachings encompass various alternatives, modifications and equivalents, as will be appreciated by those of skill in the art. Those of ordinary skill in the art having access to the teaching herein will recognize additional implementations, modifications, and embodiments, as well as other fields of use, which are within the scope of the present disclosure as described herein.

Many analytical applications, such as tissue imaging and biomarker discovery, require measurements on intact proteins over a very broad mass range. For these applications, speed of analysis can be a more important metric than the instrument's resolving power. Consequently, there is currently a need for methods and apparatus for transferring sample plates between chambers of a mass spectrometer that are faster, simpler, less expensive, and more reliable than the prior art methods and apparatus in order to improve utilization of mass spectrometer instruments. The present teaching provides a much simpler and less expensive method and apparatus for transferring sample plates from atmospheric pressure to an evacuated chamber of a mass spectrometer than the prior art methods and apparatus.

More specifically, the present teaching provides a much simpler and less expensive method and apparatus for transferring sample plates from atmospheric pressure to an evacuated chamber for analysis or processing. Many aspects of the present teaching are described in connection with a method and apparatus for transferring sample plates from atmospheric pressure to an evacuated chamber for mass spectrometry. However, it should be understood that the methods and apparatus of the present teach apply to any type of analysis and to any type of material processing that is performed under vacuum.

One aspect of the present teaching is focused on manual loading and unloading of a sample plate but it should be understood that the present teaching can be used for automatically loading and unloading sample plates as well. Features include a simplified vacuum system that requires no valves or conventional load lock chamber. One aspect of the sample plate handling of the present teaching is that some embodiments eliminate the gate valves used in prior art mass spectrometers. The gate valves in prior art mass spectrometers are needed to seal the various chambers for separate pump down cycles. The valves of prior art mass spectrometers are complex and expensive, and their use increases the processing time of the mass spectrometric analysis. Some embodiments of the sample plate handling system of the present teaching introduce new samples through a chamber with a volume that is much smaller than the volume of the analysis chamber. This reduces or eliminates the need for conventional valves and load locks because the vacuum in the analysis chamber is only minimally affected by the changes in pressure in the small-volume chamber. Furthermore, in some specific embodiments of the sample plate handling system of the present teaching, inexpensive o-rings or other vacuum seals are used to provide seals between chambers of the mass spectrometer and between the outside and the chambers.

Figure 1:
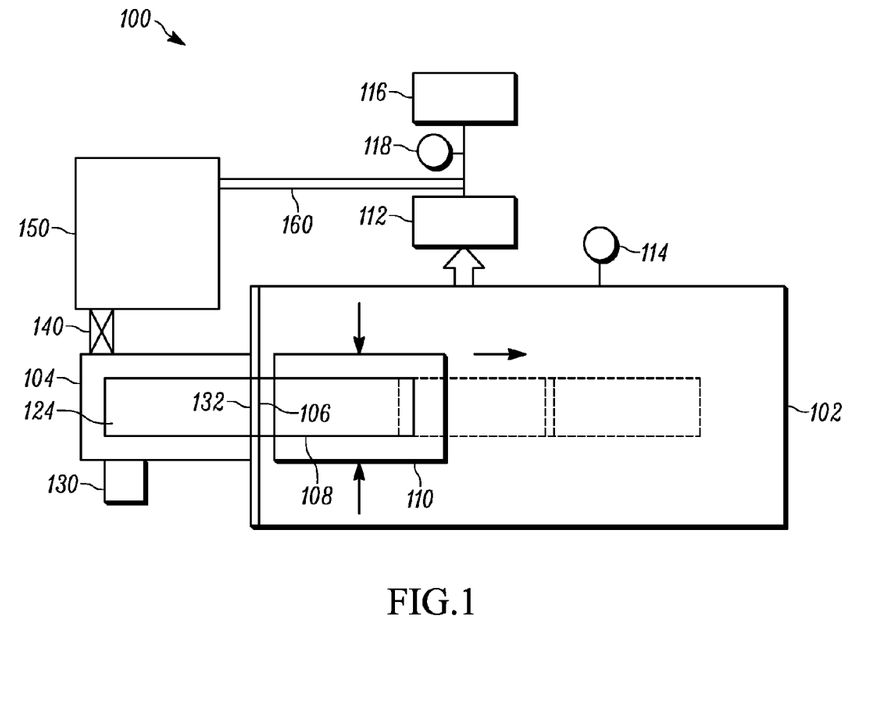
FIG. 1 illustrates a diagram for one embodiment of a sample plate handling system for a mass spectrometer, according to the present teaching.

FIG. 1 illustrates a diagram for one embodiment of a sample plate handling system for a mass spectrometer, according to the present teaching. The sample plate handling system 100 comprises a mass spectrometer chamber 102 and a transport chamber 104 connected by sealing orifice 106. A portion of the sample plate transporter 108 is mounted on a two-dimensional translation stage 110. For example, the two-dimensional translation stage can be an X-Y translation stage. Motion in the x-direction aligns the sample plate transporter 108 with orifice 106, and motion in the y-direction moves the sample plate transporter 108 so that sample plate 124, which is mounted on sample plate transporter 108, is moved through sealing orifice 106 into and out of the mass spectrometer chamber 102. The sealing orifice 106 is described in more detail in connection with FIGS. 2A and 2B.

A feature of this embodiment is that the volume of transport chamber 104 when the sample plate 124 is in the transport chamber 104 is very small compared to the volume of mass spectrometer chamber 102. In one embodiment, the volume of transport chamber 104 is less than 1 milliliter and the volume of mass spectrometer chamber 102 is greater than 10 liters. The mass spectrometer chamber 102 can be evacuated by turbomolecular pump 112 to a pressure that is less than $3\times10^{-6}$ Torr, and is backed by mechanical pump 116. Pressure in mass spectrometer chamber 102 is monitored by gauge 114, and the pressure at the mechanical pump 116 input is monitored by gauge 118.

The sample plate handling system 100 further comprises an interface 132 having a means for sealing orifice 106 when the sample plate transporter 108 is extended, so that sample plate 124 is fully within transport chamber 104. A vent valve 130 is opened to allow air to flow into transport chamber 104 when orifice 106 is sealed in order to bring the pressure in transport chamber 104 to atmospheric pressure while maintaining high vacuum in mass spectrometer chamber 102.

In some embodiments, the sample plate handling system further includes a vacuum chamber 150 that is coupled through a bypass valve 140 to the transport chamber 104. The vacuum chamber 150 is also coupled to the inlet of a mechanical pump 116 by a vacuum conduit 160. In one embodiment of the sample plate handling system according to the present teaching, the volume of the vacuum chamber 150 is very much larger than the volume of the transport chamber 104. For example, in one particular embodiment, the volume of vacuum chamber 150 is 5 L and the volume of the transport chamber 104 is less than 1 mL.

In operation of the sample plate handling system with the vacuum chamber 150, the bypass valve 140 is normally closed and remains closed while the vent valve 130 is open. After the sample plate 124 has been loaded into the transport chamber 104 and the interface 132 comprising a vacuum seal is closed, the vent valve 130 is closed and the bypass valve 140 is opened for a short time interval, such as a few seconds, which allows most of the gas initially in transport chamber 104 to be transferred to the chamber 150. Operating the sample plate handling system 100 with the chamber 150 can result in rapidly evacuation of the transport chamber 104. In various embodiments, the volume of the vacuum chamber 150 is greater than or equal to 1000 times larger than the volume of the transport chamber 104. For example, in systems where the volume of vacuum chamber 150 is 5,000 times larger than the volume of the transport chamber 104, the pressure in the transport chamber 104 is rapidly reduced to about 1/5000 of an atmosphere or about 0.15 Torr. After the bypass valve 140 is closed, the sample plate 124 is moved into the source chamber 102 after opening the vacuum seal in the interface 132. In one particular embodiment, if the volume of the source chamber 102 is 10,000 times larger than the volume of the transport chamber 104, then the maximum pressure in source chamber 102 is about 0.15/10,000 Torr or $1.5 \times 10-5$ Torr.

One feature of the sample plate handling system including the vacuum chamber 150 according to the present teaching is that the pressure in the foreline of the turbo pump remains at a pressure that is low enough for the turbo pump to operate with high efficiency. Another feature of sample plate handling system including the vacuum chamber 150 is that the maximum pressure in the source chamber 102 remains below $1.5 \times 10^{-5}$ which allows both the turbo pump and the vacuum gauge to remain on during the load cycle. Yet another feature of the sample plate handling system including the vacuum chamber 150 according to the present teaching is that it prevents the vacuum seal in the interface 132 from being contaminated by particulates swept off the sample plate 124 and then deposited on o-ring seals in the interface 132. This contamination can occur during initial transfer of air from atmospheric pressure in the transport chamber 104 to high vacuum in chamber 102. In this embodiment, the vacuum in the chamber 150 sweeps particulates to chamber 150 and deposits them where they can do no damage to the vacuum seal 132.

Figure 2A:
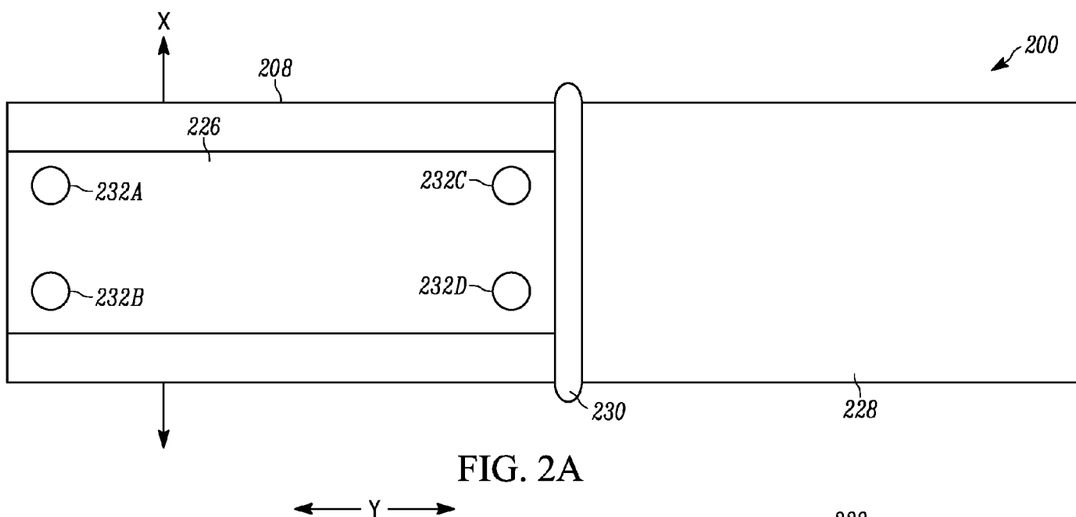
FIGS. 2A, 2B, and 2C illustrate a top-view, a side-view, and an end-view diagram of one embodiment of a sample plate transporter that is mounted on a two-dimensional translation stage, according to the present teaching.
Figure 2B:
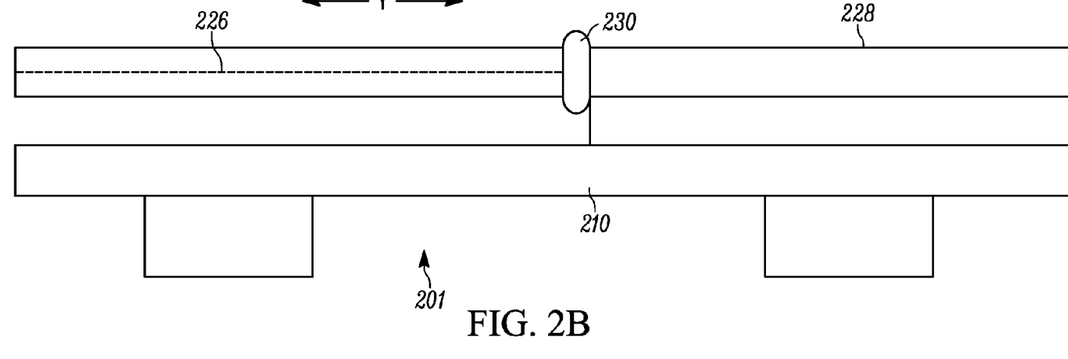
Figure 2C:
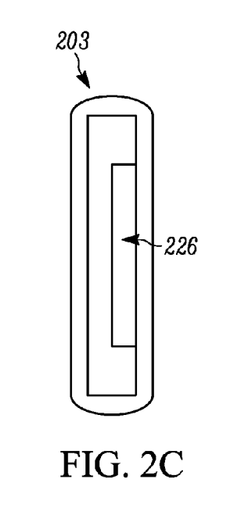

FIGS. 2A, 2B and 2C illustrate a top-view diagram 200, a side-view diagram 201, and an end-view diagram 203 of one embodiment of a sample plate transporter 208 that is mounted on X-Y stage 210, according to the present teaching. The transporter 208 includes a sample plate receiver 226. A first portion 228 of the transporter 208 is attached to X-Y stage 210, as shown in FIG. 2B. An o-ring 230 or other type of vacuum seal surface is positioned between the sample plate receiver 226 and the first portion 228 of the sample plate transporter 208 that is attached to X-Y table 210.

FIG. 1 and FIG. 2A show that in the extended position of sample plate transporter 108 the sample plate receiver 226 is fully within transport chamber 104. In this configuration, an o-ring 230 forms a vacuum sealing surface that engages with sealing orifice 106 and seals the orifice 106 so that, even if the pressure difference between mass spectrometer chamber 102 and the transport chamber 104 is one atmosphere, there is no significant flow of gas between the two chambers. In some embodiments, the o-ring 230 is mounted on transporter 208 in a groove located between sample plate receiver 226 and the first portion 228, as shown in FIG. 2A, and a mating sealing surface is provided within orifice 106. In an alternative embodiment, o-ring 230 is mounted in a groove in orifice 106, and a mating surface replaces o-ring 230 on sample plate transporter 208.

The sample plate receiver 226 uses magnets to capture the sample plates. The sample plates are manufactured with at least some magnetic material so that they are physically attracted to the magnets. In the embodiment shown in FIG. 2A, the sample plate receiver 226 includes permanent magnets 232A, 232B, 232C, and 232D mounted in the surface of sample plate receiver 226.

Figure 3A:
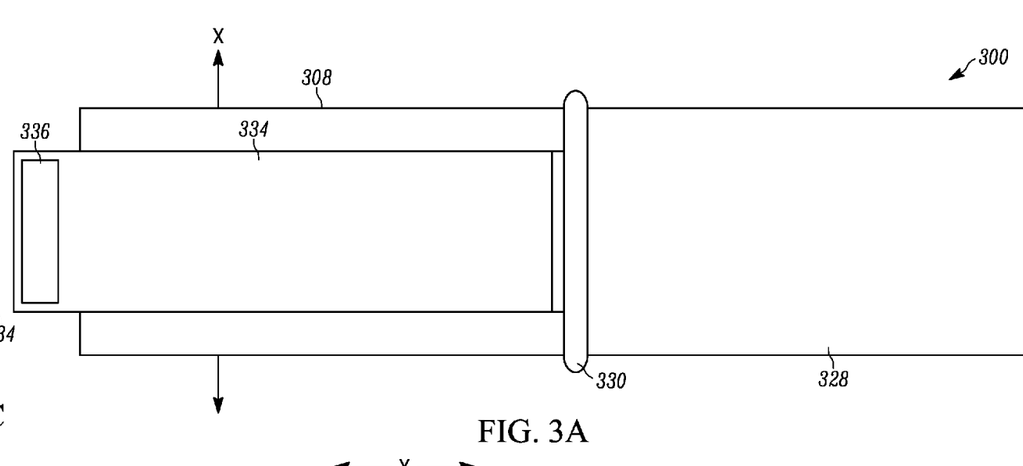
FIGS. 3A, 3B, and 3C illustrate a top-view diagram, a side-view diagram, and an end-view diagram of an embodiment of a sample plate transporter with a sample plate mounted on the transporter, according to the present teaching.
Figure 3B:
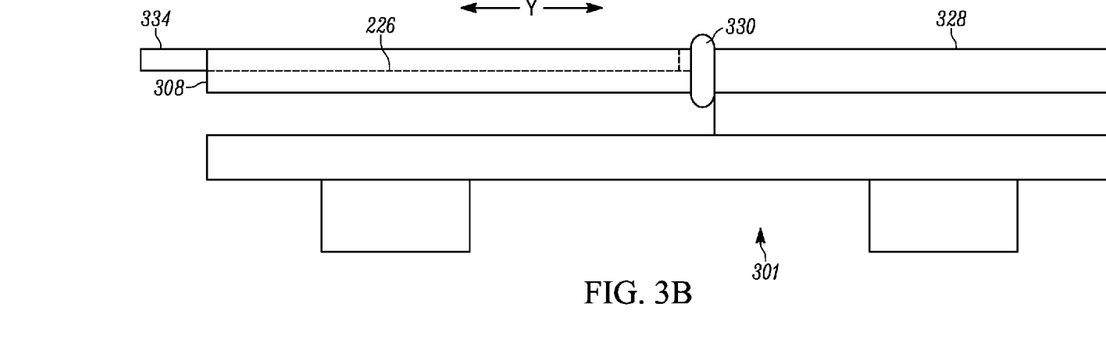
Figure 3C:
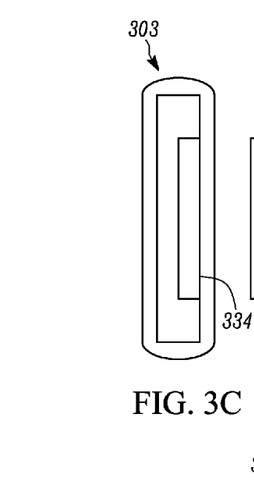

FIGS. 3A, 3B, and 3C illustrate a top-view diagram 300, a side-view diagram 301, and an end-view diagram 303 of an embodiment of a sample plate transporter with a sample plate mounted on the transporter, according to the present teaching. Referring to FIGS. 2A, 2B, and 2C and to FIGS. 3A, 3B, and 3C, a sample plate 334 is positioned on sample plate receiver 226, as described in connection with FIGS. 2A-C. The sample plate 334 is held onto the sample pate receiver 226 with the magnets 232A, 232B, 232C, and 232D mounted in the surface of sample plate receiver 226. As shown in the side-view diagram 301 of FIG. 3B, the sample plate 334 is mounted such that the top of the sample plate 334 is flush with the top of the sample plate transporter 308. This positioning of the sample plate 334 on the sample plate receiver 226 advantageously minimizes the size of the orifice 106 (see FIG. 1) required to pass the sample plate 334 from the transport chamber 104 to the mass spectrometer chamber 102. It may be desirable in some systems to include a bar code 336 that is positioned proximate to one end of sample plate 334 for identification. Samples for analysis are typically distributed in predetermined positions on the sample plate 334 for analysis.

FIGS. 3A, 3B, and 3C illustrate that one end of the sample plate 334 extends beyond the end of sample transporter 308. Referring now to both FIG. 1 and FIGS. 3A, 3B, and 3C, the X-Y stage 110 in the mass spectrometer chamber 102 also moves the sample transporter 108 to align the transporter 308 with the orifice 106 in the X direction, and to move the transporter 308 in the Y direction to transport the sample plate 124 from the transport chamber 104 to the mass spectrometer chamber 102. When the sample plate 124 is fully in the transport chamber 104, the o-ring 330 seals the orifice 106 to isolate the mass spectrometer chamber 102 from the transport chamber 104. The transport chamber 104 can then be vented to atmosphere by opening valve 130 without affecting the pressure in the mass spectrometer chamber 102.

Figure 4A:
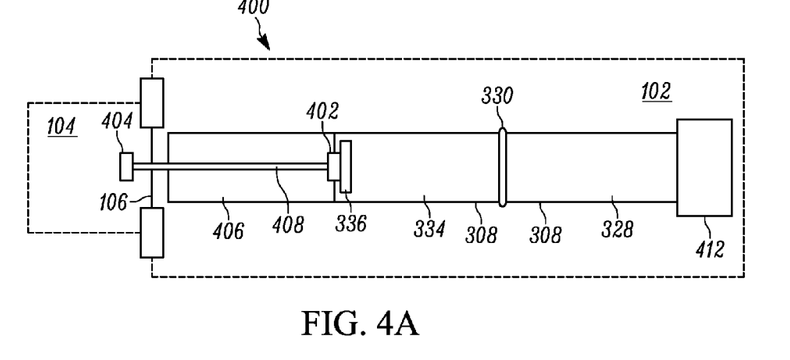
FIGS. 4A, 4B, and 4C illustrate top-view diagrams of an embodiment of the sample plate handling system in various positions in the sample plate transporter described in connection with FIGS. 1, 2A, and 3A.
Figure 4B:
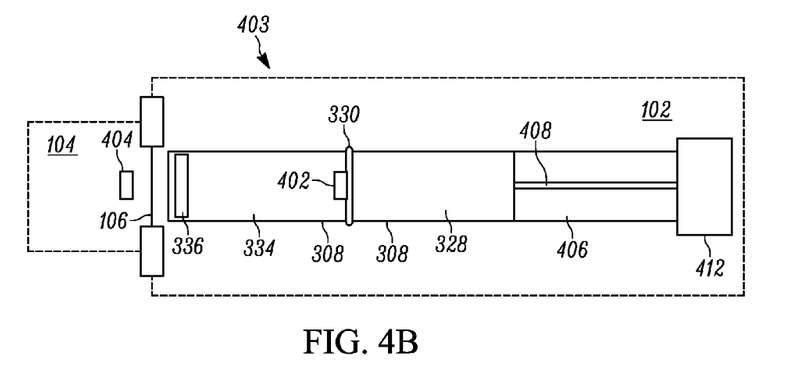
Figure 4C:
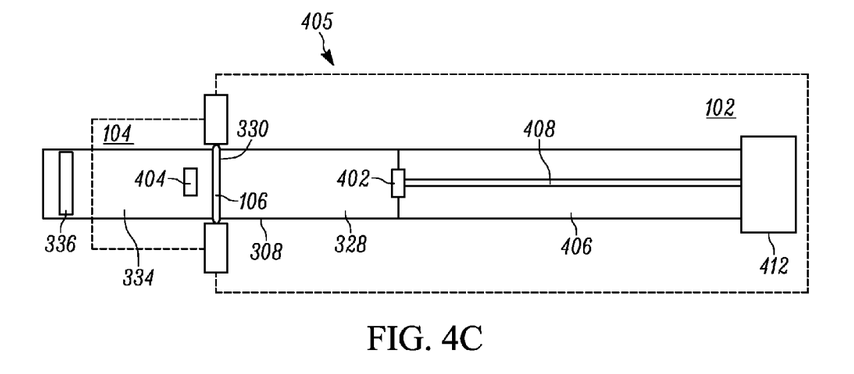

FIGS. 4A, 4B, and 4C illustrate top-view diagrams of an embodiment of the sample plate handling system, according to the present teaching, in various positions of the sample plate transporter 308 described in connection with FIGS. 3A, 3B, and 3C. In FIG. 4A, the top-view diagram 400 shows that the sample plate transporter 308 is fully in the mass spectrometer chamber 102 in the Y direction. In FIG. 4B, the top-view diagram 403 shows that the sample plate transporter 308 is mid-way in the mass spectrometer chamber 102 in the Y direction. In FIG. 4C, the top-view diagram 405 shows that the sample plate transporter 308 is partially in the transport chamber 104 in the Y direction. This is the sample load position.

Figure 5A:
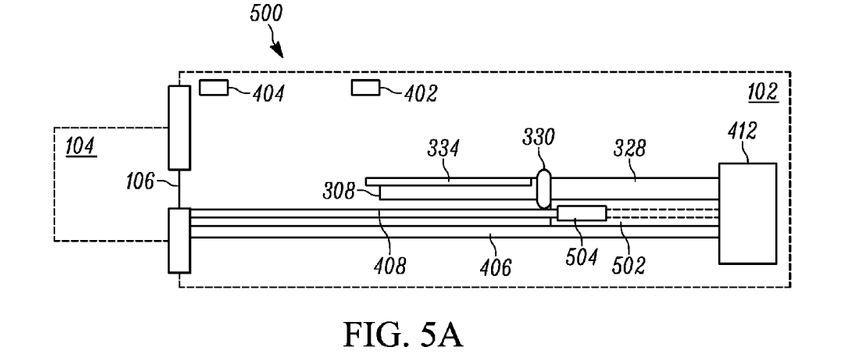
FIGS. 5A, 5B, and 5C illustrate side-view diagrams of an embodiment of the sample plate handling system according to the present teaching in various positions in the sample plate transporter.
Figure 5B:
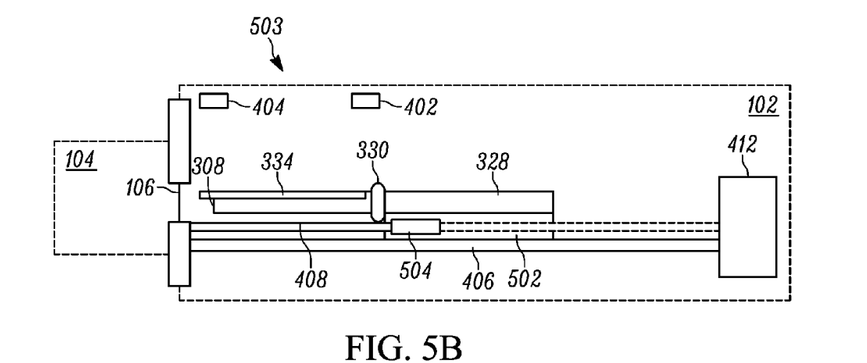
Figure 5C:
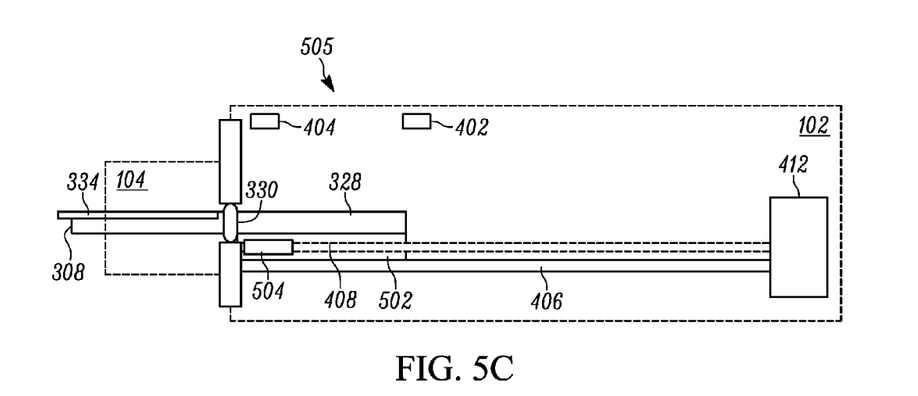

FIGS. 5A, 5B, and 5C illustrate side-view diagrams of an embodiment of the sample plate handling system, according to the present teaching, showing various positions of the sample plate transporter described in connection with FIGS. 3A, 3B, and 3C. In FIG. 5A, the top-view diagram 500 shows that the sample plate transporter 308 is fully in the mass spectrometer chamber 102 in the Y direction. In FIG. 5B, the top-view diagram shows that the sample plate transporter 308 is mid-way in the mass spectrometer chamber 102 in the Y direction. In FIG. 5C, the top-view diagram shows that the sample plate transporter 308 is partially in the transport chamber 104 in the Y direction. FIGS. 4A, 4B, and 4C and FIGS. 5A, 5B, and 5C together illustrate the motions of the sample plate handling system in the X and Y directions.

Referring to FIGS. 1, 3A-3C, 4A-4C, and 5A-5C, the mass spectrometer chamber 102 comprises an ion source chamber of a mass spectrometer that includes an ion source, such as a laser 402, which ionizes a sample of interest on a sample plate 334 positioned therein. In some systems according to the present teaching, the transport chamber 104 also includes a bar code reader 404 for reading the bar codes 336 on the sample plates 334. The laser 402 is positioned to ionize the sample of interest on sample plate 334. The X-Y stage 110 in the mass spectrometer chamber 102 moves the sample plate transporter 308 to a position transverse to the ion optic axis of the mass spectrometer traverse and to the output of the laser 402. The X-Y stage is used to align sample positions on the sample plate 334 with the laser beam generated by the laser 402.

FIGS. 4A-C and 5A-C illustrate the range in the Y direction of the sample test position of the X-Y stage 110 in the mass spectrometer chamber 102. FIGS. 4A-C and FIGS. 5A-C also illustrate the alignment of the sample plate transporter 308 with the orifice 106 in the X direction. In addition, the X-Y stage 110 in the mass spectrometer chamber 102 moves the sample plate transporter 308 in the Y direction in order to move the sample plate 334 from the transport chamber 104 to the mass spectrometer chamber 102. Referring to FIGS. 4C and 5C and also to FIG. 1 and FIGS. 3A-C, when the sample plate 334 is fully in the transport chamber 104, the o-ring 330 on the sample plate transporter 308 seals the orifice 106 to isolate the mass spectrometer chamber 102 from the transport chamber 104. FIGS. 4C and 5C illustrate the load position of the sample plate transporter 308. The transport chamber 104 can then be vented to atmosphere without affecting the pressure in the mass spectrometer chamber 102.

As shown in FIGS. 4A-4C and FIGS. 5A-5C, the sample plate handling system comprises a fixed slide 406 that supports the motion of the sample plate transporter 308 in the Y direction. The fixed slide 406 includes an Acme screw 408, which is a threaded rod that is used to translate the sample plate transporter 308 in the Y direction. A stepper motor 412 is used to control the motion of the Acme screw 408. The motion in the X direction is also controlled by a slide mechanism, which, in one embodiment, is an Acme screw and stepper motor (not shown).

FIGS. 5A-5C illustrate a fixed slide 406 and a moving slide 502. The moving slide 502 comprises an Acme nut 504 that surrounds the Acme screw 408. In some embodiments, the stepper motor turns the Acme screw, and this motion causes the Acme nut 504 to move along the direction of the Acme screw. The moving slide 502 is fixed to the portion 328 of the sample plate transporter 308 that is attached to the X-Y stage 110 (FIG. 1) such that moving slide 502 moves together with the sample plate transporter 308.

One aspect of the present teaching is that only two stepper motors are needed to control the motion of the X-Y stage 110, one for the X direction and one for the Y direction. Using only two stepper motors reduces the complexity of the mass spectrometer sample transport system according to the present teaching. Also, the apparatus for transporting samples, according to the present teaching, are compatible with the ion optics of many known prior art mass spectrometers. Therefore, the methods and apparatus for transporting samples, according to the present teaching, are easily adapted into existing mass spectrometer systems.

Another aspect of the present teaching is that the load lock required for many prior art mass spectrometers can be eliminated. Load locks are vacuum sample staging and entry systems that are commonly used to couple samples from atmosphere to vacuum. Known load lock systems for mass spectrometers include a sample staging chamber, a gate valve, a transport mechanism to move the sample to and from the load lock, an access door, and ports coupled to a vacuum pump for evacuating the chambers. One significant feature of the present teaching is that complex load lock systems commonly used in known mass spectrometer systems can be replaced by a simple door with a venting system, as described in connection with the present teaching.

Figure 6A:
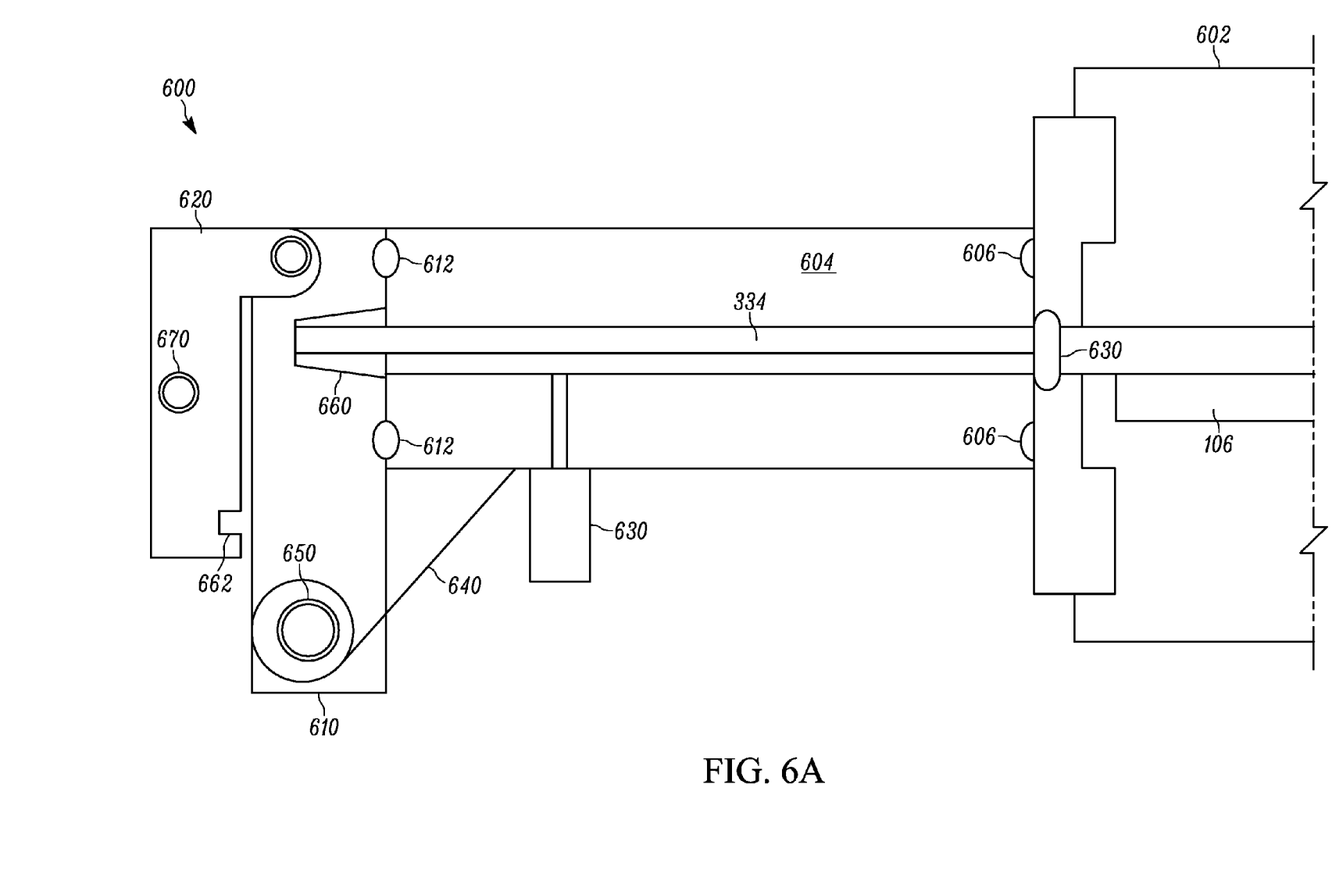
FIG. 6A illustrates a side-view of the sample plate handling system for a mass spectrometer according to the present teaching that includes a transport chamber and a door that supports loading and unloading of samples into and out of the transport chamber.

FIG. 6A illustrates a side-view of a sample plate handling system for a mass spectrometer, according to the present teaching, that includes a transport chamber 604 and a door 610 that supports loading and unloading of samples into and out of the transport chamber 604. One feature of the transport chamber 604 shown in FIG. 6A is that the void volume when the sample transporter 308 in the sample load position (FIG. 4C) is very small. In one embodiment, this void volume is less than 1 milliliter. One end of the transport chamber 604 is sealed to the wall of the mass spectrometer chamber 602 by an o-ring 606, and the other end of the transport chamber 604 is sealed to the door 610 by a second o-ring 612. The door 610 includes a spring-loaded mechanism 650 and a rigid support 640 that maintains the door 610 in the closed position.

Referring back to FIGS. 1, 2A-C, and 3A-C, a slot 660 in the door 610 allows one end of sample plate 334 to extend beyond the end of the transport chamber 604 when the door is closed. When the sample transporter 308 is in the load position and orifice 106 is sealed, the vent valve 630 can be activated to bring the pressure in the transport chamber 604 to atmospheric pressure without affecting the pressure in the mass spectrometer chamber 602.

Figure 6B:
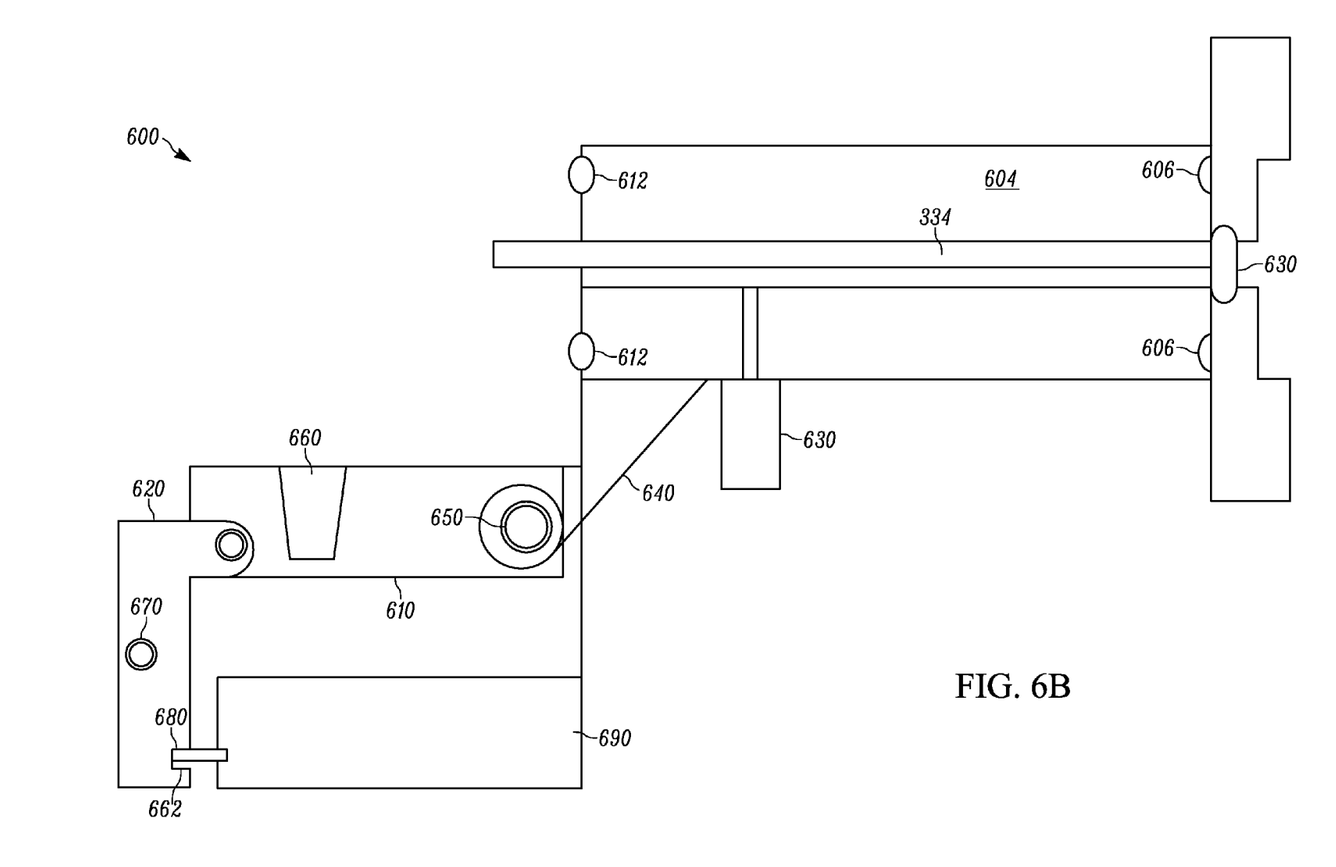
FIG. 6B illustrates a side-view of the sample plate handling system described in connection with FIG. 6A with the door opened.

FIG. 6B illustrates a side-view of the sample plate handling system described in connection with FIG. 6A with the door 610 opened. One end of the sample plate 334 (FIGS. 3A-B) is exposed so that the sample plate 334 can be manually removed and replaced by a new sample plate containing samples of interest to be analyzed. In one embodiment, the door 610 can be opened by manually grasping a handle bar 670 attached to handle 620 and pulling out and then down on the handle. The door 610 is then locked open by engaging slot 662 with pin 680 mounted on rigid support 690. When a new sample plate is loaded onto transporter 108 (FIG. 1), the door 610 is then closed by manually pulling on handle bar 670 to disengage slot 662 with pin 680. The spring-loaded mechanism 650 then closes the door 610 and provides sufficient pressure on o-ring 612 to seal the door 610 to the transport chamber 604. One skilled in the art will appreciate that there are numerous variations of door 610 opening and closing mechanisms according to the present teaching, and that the present teaching is not limited to the mechanisms shown in FIG. 6A-B.

One feature of the sample plate handling system of the present teaching is that there are various manual, semi-automated, or fully automated sample plate loading and unloading configurations. In particular, some embodiments of the present teaching only allow manual loading and unloading of a single sample plate, while other embodiments of the present teaching provide semi or fully automated loading and unloading of sample plates that reduces the amount of technician time required for performing analysis. Semi or fully automated loading and unloading of sample plates can be accomplished by replacing the door 610 that supports loading and unloading of samples with an automated gate valve, and adding an automated mechanism that sequentially supplies and removes sample plates in place of the manual step employed in the present teaching.

For many applications it is desirable for the sample plate handling system of the present teaching to be semi or fully automated. These semi and fully automated systems are usually computer controlled. Referring to FIGS. 1, 2, and 6A-B, a LOAD command can be issued to the computer that causes the vent valve 630 to close and the X-Y stage 110 to retract the sample plate transporter 108, opening the orifice 106 between the transport chamber 104 and mass spectrometer chamber 102. In one embodiment, a camera is installed with a view of the transport chamber 104 that records an image of sample plate 334 as it is loaded or ejected. The resulting image of the bar code 336 on plate 334 can be read and recorded and then associated with a particular mass spectrum. In one embodiment, the transport chamber is constructed from transparent plastic such as polycarbonate to facilitate recording of an image of sample plate 334, and also to facilitate reading and recording the associated bar code 336.

A feature of the sample plate handling system of the present teaching is that the volume of the mass spectrometer chamber 102 is several orders of magnitude larger than the volume of the transport chamber 104. In one embodiment of the present teaching, the ratio of the volume of the mass spectrometer chamber 102 to the volume of the transport chamber 104 is greater than 10,000. Consequently, after transferring a sample plate 334 into and out of the mass spectrometer, the pressure in the mass spectrometry chambers 102 very rapidly reaches the operating pressure with modern vacuum pumps, such as the turbomolecular pump 112. Such vacuum pumps operate with high efficiency while evacuating high pressures in small volumes. The maximum initial pressure in the transport chamber 104 following a plate loading is typically less than $10^{-4}$ atmospheres or less than 0.076 Torr. Consequently, the vacuum level of the mass spectrometer chamber 102 can return very quickly to a desired operating pressure of approximately $10^{-6}$ Torr. This feature of the sample handling system of the present teaching greatly reduces the time for sample analysis.

Another feature of the sample transport system of the present teaching is that any size or type of sample plate may be used. This includes sample plates such a microscope slides, Hudson plates, microtiter plates, or other sample plates known in the art. One skilled in the art will appreciate that the sample plate handing system of the present teaching may be easily adapted to any sample plate template.

Figure 7:
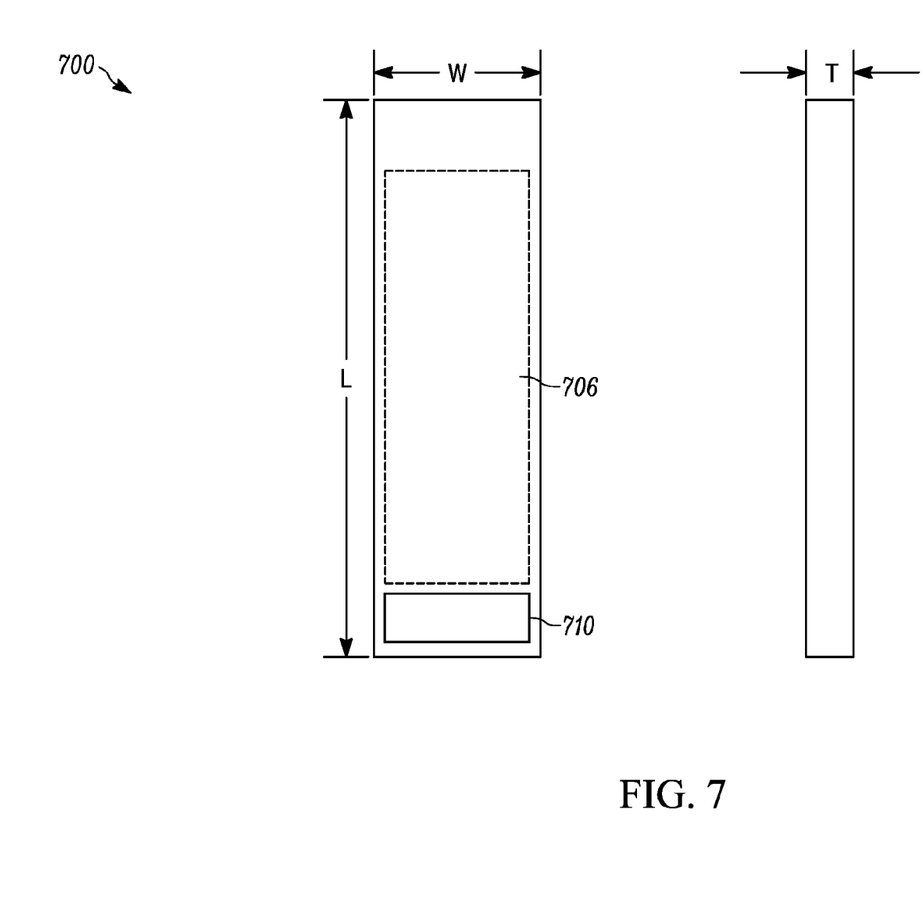
FIG. 7 illustrates an embodiment of a sample plate, according to the present teaching.

FIG. 7 illustrates one embodiment of a sample plate 700 according to the present teaching. In some embodiments, the sample plate 700 is formed from magnetic material, such as 400-series stainless steel, but one skilled in the art will appreciate that many other materials can be used. In one particular embodiment, the dimensions of the sample plate 700 are approximately 86 mm long, 27 mm wide, and 6 mm thick. Samples for analysis are deposited on surface 706 of the sample plate. In some embodiments, samples are deposited in a predetermined array on the surface of the plate. In other embodiments, samples are deposited on an alternate plate, such as a glass microscope slide, or on any other material that is rendered electrically conductive, and this alternative plate is mounted in an appropriate holder on the sample plate 700.

One feature of the sample transport system of the present teaching is that any plate size or sample template can be used. This includes plates that range from a full microtiter plate size that accommodates 384 or 1536 sample spots, to a small chip that accommodates only one sample to be analyzed. In various embodiments, the sample plate 700 can include a bar code 710 that can be read by the mass spectrometer to identify information about the sample and its distribution on the sample plate, as specified by the user.

In some applications of mass spectrometers, the time required to collect and prepare samples and to deposit samples onto the sample plate 334 is long compared to the time required to analyze the samples in the mass spectrometer. In other applications, so-called high-throughput applications, large numbers of samples can be prepared very rapidly using robotic liquid handlers and the throughput is determined by the total time required to load and analyze the samples. The methods and apparatus for transporting samples in a mass spectrometer according to the present teaching provide optimum performance for a wide range of applications. For high throughput applications, it is important to begin mass spectrometric analysis as quickly as feasible following loading of a sample plate. One feature of the sample plate handling systems according to the present teaching is that the dead time between presenting a sample to the plate receiver at atmospheric pressure and beginning the mass spectrometric analysis is an insignificant time relative to the time required for the analysis. In many embodiments, the dead time can be 10 seconds or less.

EQUIVALENTS

While the Applicants' teaching is described in conjunction with various embodiments, it is not intended that the Applicants' teaching be limited to such embodiments. On the contrary, the Applicants' teaching encompass various alternatives, modifications, and equivalents, as will be appreciated by those of skill in the art, which may be made therein without departing from the spirit and scope of the teaching.

What is claimed is:
1. A sample plate handling system for a time-of-flight mass spectrometer, the sample plate handling system comprising:
   a) a transport chamber;
   b) a vacuum chamber that is coupled through a bypass valve to the transport chamber;
   c) a mass spectrometer chamber that is mechanically coupled to the transport chamber;
   d) a two-dimensional translation stage that is positioned in the mass spectrometer chamber;
   e) a sample plate transporter mounted on the two-dimensional translation stage, the sample plate transporter comprising a first portion mechanically attached to the two-dimensional translation stage; a second portion defining a sample plate receiver that is positioned in the transport chamber when loading and unloading samples, and a sealing surface located between the first and the second portions; and
   f) a sealing orifice connecting the transport chamber and the mass spectrometer chamber, wherein a motion of the two-dimensional translation stage in one direction aligns the sample plate transporter with the sealing orifice and a motion of the two-dimensional translation stage in the other direction moves the sealing surface of the sample plate transporter to engage the sealing orifice, thereby preventing gas flow between the mass spectrometer chamber and the transport chamber.

2. The sample plate handling system of claim 1 wherein the mass spectrometer chamber comprises an ion source that ionizes a sample of interest on a sample plate positioned on the sample plate transporter.

3. The sample plate handling system of claim 2 wherein the ion source comprises a laser that generates an ionizing laser beam.

4. The sample plate handling system of claim 3 wherein the two-dimensional translation stage positions the sample plate transporter so that a sample to be ionized is positioned in a path of the ionizing laser beam.

5. The sample plate handling system of claim 1 wherein a sample plate that supports samples for analysis is positioned in the sample plate receiver so that the sample plate is flush with a top portion of the sample plate receiver.

6. The sample plate handling system of claim 1 wherein the sample plate receiver comprises at least one magnet and a sample plate is formed of a magnetic material that is attracted to the at least one magnet in the sample plate receiver so that the sample plate is secured to the sample plate receiver.

7. The sample plate handling system of claim 1 wherein the sealing orifice comprises a vacuum o-ring seal.

8. The sample plate handling system of claim 1 wherein the two-dimensional translation stage comprises an Acme screw that passes through an Acme nut that translates the second portion of the sample plate transporter into and out of the mass spectrometer chamber.

9. The sample plate handling system of claim 8 further comprising a stepper motor that turns the Acme screw.

10. The sample plate handling system of claim 1 wherein a volume of the transport chamber is at least 10,000 times smaller than a volume of the mass spectrometer chamber.

11. The sample plate handling system of claim 1 further comprising a door that seals an end of the transport chamber.

12. The sample plate handling system of claim 11 wherein the door is manually operated.

13. The sample plate handling system of claim 11 wherein the door is automatically controlled.

14. The sample plate handling system of claim 11 wherein the door further comprises a slot that allows one end of a sample plate to extend beyond the end of the transport chamber when the door is closed.

15. The sample plate handling system of claim 1 further comprising a bar code reader positioned to read bar codes on a sample plate.

16. The sample plate handling system of claim 15 wherein the bar code reader is positioned in the transport chamber.

17. The sample plate handling system of claim 15 wherein the bar code reader is positioned adjacent to the transport chamber.

18. The sample plate handling system of claim 1 further comprising a vacuum pump that controls pressure inside the mass spectrometer chamber.

19. The sample plate handling system of claim 18 wherein the vacuum pump comprises a turbomolecular vacuum pump backed by mechanical vacuum pump.

20. The sample plate handling system of claim 1 further comprising a vent valve positioned in the transport chamber that can be opened to allow air to flow into the transport chamber when the sealing orifice is sealed to bring the pressure in the transport chamber to atmospheric pressure while maintaining high vacuum in the mass spectrometer.

21. The sample plate handling system of claim 1 further comprising a vacuum pump having an inlet that is coupled to the vacuum chamber through a conduit.

22. The sample plate handling system of claim 21 wherein the vacuum pump also back a turbomolecular pump that evacuates the mass spectrometer chamber.

23. The sample plate handling system of claim 21 wherein the vacuum pump comprises a mechanical vacuum pump.

24. The sample plate handling system of claim 21 wherein a volume of the vacuum chamber is greater than or equal to 1,000 times a volume of the transport chamber.

25. The sample plate handling system of claim 21 wherein a volume of the vacuum chamber is greater than or equal to 5,000 times a volume of the transport chamber.

26. A method of transporting samples into and out of a time-of-flight mass spectrometer, the method comprising:
   a) positioning samples to be analyzed on a sample plate;
   b) positioning the sample plate having the samples to be analyzed in a sample plate receiver;
   c) positioning the sample plate receiver into a sample plate transporter that translates through a transport chamber;
   d) opening a bypass valve coupled between a vacuum chamber and the transport chamber after positioning the sample plate receiver into the sample plate transporter, thereby allowing gas initially in the transport chamber to be transferred to the vacuum chamber;
   e) closing the bypass valve and then opening a sealing orifice;
   f) translating the sample plate receiver through the sealing orifice and into a mass spectrometer chamber with the sample plate transporter, wherein the sealing orifice provides a vacuum seal that substantially prevents gas flow between the transport chamber and the mass spectrometer chamber; and
   g) translating the sample plate receiver back through the sealing orifice and into the transport chamber with the sample plate transporter after analysis.

27. The method of claim 26 wherein the translating the sample plate receiver through the sealing orifice and into the mass spectrometer chamber comprises first aligning the sample plate transporter with the sealing orifice in a first direction and then linearly translating the sample plate receiver through the sealing orifice and into the mass spectrometer chamber with the sample plate transporter.

28. The method of claim 26 wherein the sample plate is positioned flush with the sample plate transporter.

29. The method of claim 26 wherein a time required to transfer a sample from atmospheric pressure to a predetermined operating pressure in the transport chamber is less than ten seconds.

30. The method of claim 26 wherein the sample plate having the samples to be analyzed is positioned in the sample plate receiver by magnetically attracting the sample plate to the sample plate receiver.

31. The method of claim 26 wherein the translating the sample plate receiver through the sealing orifice and into the mass spectrometer chamber with the sample plate transporter and the translating the sample plate receiver back through the sealing orifice and into the transport chamber with the sample plate transporter comprises translating with a translation stage comprising an Acme screw that passes through an Acme nut.

32. The method of claim 26 wherein the transport chamber has a volume that is at least 10,000 times smaller than a volume of the mass spectrometer chamber.

33. The method of claim 26 further comprising closing a door that seals an end of the transport chamber.

34. The method of claim 33 wherein the door is automatically controlled.

35. The method of claim 26 further comprising providing a bar code to the sample plate.

36. The method of claim 35 further comprising reading the bar code on the sample plate and associating the bar code with a mass spectrum generated by the time-of-flight mass spectrometer.

37. The method of claim 26 further comprising controlling pressure inside the mass spectrometer chamber with a vacuum pump while the sample plate receiver is translated though the sealing orifice.

* * * * *